United States Patent [19]

Salzbrunn et al.

[11] Patent Number: 4,876,196
[45] Date of Patent: Oct. 24, 1989

[54] METHOD OF CONTINUOUSLY PRODUCING ETHANOL FROM SUGAR-CONTAINING SUBSTRATES

[75] Inventors: Wolfgang Salzbrunn, Neustadt; Eva Steiner, Korneuburg; Wilfried Wöhrer, Bad Vöslau; Otto Meixner, Vienna, all of Austria

[73] Assignee: Vogelbusch Gesellschaft m.b.H., Austria

[21] Appl. No.: 149,955

[22] Filed: Jan. 27, 1988

Related U.S. Application Data

[63] Continuation of Ser. No. 783,923, Oct. 3, 1985, abandoned.

[30] Foreign Application Priority Data

Oct. 18, 1984 [AT] Austria .................. A 3318/84

[51] Int. Cl.$^4$ ...................... G12P 7/06; G12P 7/14
[52] U.S. Cl. .................... 435/161; 435/162; 435/813; 435/222
[58] Field of Search ............ 435/161, 162, 813, 822

[56] References Cited

U.S. PATENT DOCUMENTS

| | | | |
|---|---|---|---|
| 4,310,629 | 1/1982 | Muller et al. | 435/162 |
| 4,403,034 | 9/1983 | Rogers et al. | 435/161 |
| 4,413,058 | 11/1983 | Arcuri et al. | |
| 4,443,544 | 3/1984 | Rogers et al. | 435/162 |

FOREIGN PATENT DOCUMENTS

0047641 4/1984 European Pat. Off. .
3148329 8/1982 Fed. Rep. of Germany .

OTHER PUBLICATIONS

Cysewski et al., *Biotechnology and Bioengineering*, vol. XX, (1978), pp. 1421-1444.

Karsch et al., "Ethanol Production by Zymomonas and Saccharomyces", *Applied Microbiology and Biotechnology*, Spranger-Vertag, 1983.

Rogers et al., "Ethanol Production by *Zymomonas mobilis*", *Advances in Biochemical Engineering*, vol. 23.

W. Kuhlmann et al., "Reaktionstechnische Aspekte der Ethanolproduktion in einer Dreistufigen Ruhrkesselreaktorkaskade Ohne und mit Zellruckfuhrung", Symposium Technische Mikrobiologie, Berlin, (1982).

K. Rosen, "Continuous Production of Alcohol", *Process Biochemistry*, 5/78, pp. 25-26.

Fein et al., "High Productivity Continuous Ethanol Fermentation with a Flocculating Mutant Strain of *Zymomonas mobilis*", *Biotechnology Letters*, vol. 5, No. 1, 1983, pp. 19-24.

Klein et al., "Improvement of Productivity and Efficiency in Ethanol Production with Ca-Alginate Immobilized *Zymomonas mobilis*", *Biotechnology Letters*, vol. 5, No. 8, (1983), pp. 497-502.

Lee et al., "Biotechnology Letters", vol. 3, No. 4, pp. 177-182, (1981).

*Primary Examiner*—Charles F. Warren
*Assistant Examiner*—Irene Marx
*Attorney, Agent, or Firm*—Ostrolenk, Faber, Gerb & Soffen

[57] ABSTRACT

In a method of continuously producing ethanol from sugar-containing substrates by fermentation of sugars by means of a flocculating strain of *Zymomonas mobilis* under anaerobic conditions and at a pH of from 4.5 to 7 a substrate is led commonly with *Zymomonas mobilis* cells through at least three fermentation stages without preceding sterilization, a concentration of at least 4% by volume of ethanol is maintained in each fermentation stage, a residence time of the fermentation medium in the entire system of maximally 3⅓ h corresponding to a dilution rate of the fermentation medium in the entire system of at least 0.3 h$^{-1}$ is adjusted, the *Zymomonas mobilis* cells are separated by sedimentation after the final fermentation stage, the *Zymomonas mobilis* cells are recycled into the first fermentation stage, and the ethanol-containing substrate separated from the *Zymomonas mobilis* cells is drawn off.

7 Claims, 1 Drawing Sheet

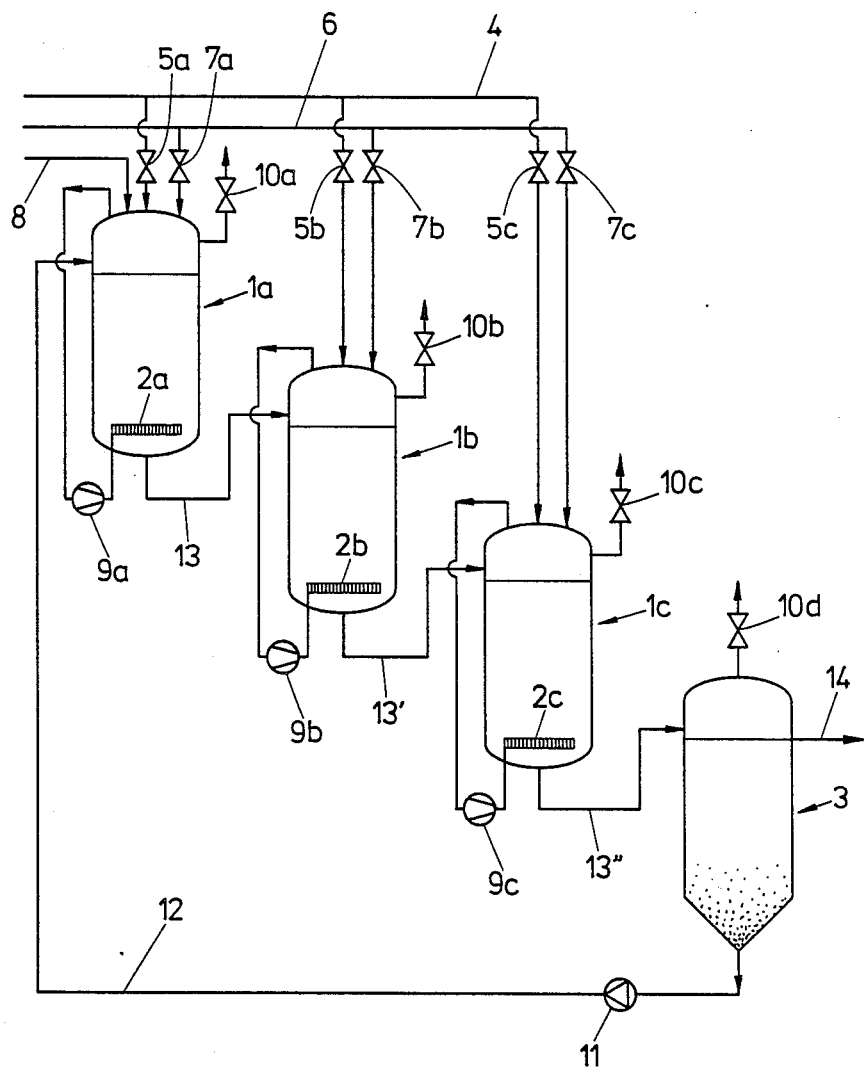

METHOD OF CONTINUOUSLY PRODUCING ETHANOL FROM SUGAR-CONTAINING SUBSTRATES

This application is a continuation of application Ser. No. 783,923, filed Oct. 3, 1985, now abandoned.

The invention relates to a method of continuously producing ethanol from sugar-containing substrates by fermentation of the sugars by means of a fluctuating strain of Zymomonas mobilis under anaerobic conditions and at a pH of from 4.5 to 7.

A method of this kind is known from U.S. Pat. No. 4,413,058. Therein, an slantedly positioned tube reactor is used, at whose lower end the sugar-containing substrate is fed and in whose upper end region the fermented ethanol-containing substrate is discharged. The flow rate is adjusted such that the conversion of sugar to ethanol is ensured, yet that the used culture of a fluctuating strain of Zymomonas mobilis, i.e. Zymomonas mobilis "f" NRRLB 12526 is by no means discharged from the reactor. Almost over its entire length, the tube reactor is provided with a series of $CO_2$ discharge openings, conduits each leading away therefrom. The free ends of these conduits open into the surrounding air approximately at the height of the upper end of the tube reactor or sightly thereabove. The mouths of the conduits are closed, e.g., by cotton wads.

Since the microorganism culture must not be discharged, with the known method the flow rate of the substrate must be very closely monitored.

The construction of the tube reactor used is so complex that its application on a technical scale is not possible at all or with very great difficulties only. Furthermore, plants already existing and having conventional fermentors would have to be completely replaced, resulting in especially high investment costs.

Also according to German Offenlegungsschrift No. 1 48 329, a flocculating strain, i.e. Zymomonas mobilis ATCC 31822, obtained by selection from strain ATCC 31821, is used for producing ethanol from a carbohydrate substrate. The method disclosed is, however, only semi-continuous. At first, an inocculated fermentation medium is shaken in a fermentor. When the carbon dioxide development has stopped, the bacteria cell colonies are allowed to settle, the ethanol-containing supernatant is drawn off and replaced by fresh fermentation medium.

A two-step fermentation process for producing ethanol by using Zymomonas mobilis strains, i.e. ATCC 29191 and ATCC 10988, is furthermore disclosed in European patent specification No. 0 047 641, wherein a bacteria cell suspension is produced in the first step, and ethanol is produced in the second step by adding fermentable sugar to that suspension. In the second step, only a slight bacteria cell reproduction is to occur. Flocculating Zymomonas mobilis strains are not considered, and thus a separation of the bacteria cultures used, from the fermentation medium by sedimentation is not possible on an industrial scale, but energy and time consuming centrifugation or filtering methods must be utilized for this purpose.

A serious disadvantage common to all the known methods listed is that it is absolutely necessary to use sterilized substrates. The expenditure connected with a fermentation procedure under sterile conditions very much reduces the economy of such a method, a fact that is also clearly expressed in the article 37 Ethanol production by Zymomonas and Saccharomyces, Advantages and Disadvantages" in Eur. Jour. of Applied Microbiology and Biotechnology, 18, 1983, pp. 387–391.

If one were to work in accordance with the known methods without sterilization, there would be the great risk of an infection, particularly by lactic bacteria or by yeasts, which - similar to Zymomonas mobilis - are ethanoltolerant even up to concentrations of approximately 15 percent by volume.

Zymomonas mobilis has a specific ethanol production rate that is two to three times that of yeast, with simultaneously higher yields, and furthermore it does not require oxygen for its growth, whereas yeast must be at least slightly aerated for a sufficient production of biomass.

For enabling a utilization of these attractive advantages of Zymomonas mobilis also for the production of ethanol on an industrial scale, the invention has as its object to overcome the above-mentioned disadvantages and difficulties of the known methods and to provide an operationally safe method which does without a sterilization of the substrates and for whose execution also existing fermentation plants are excellently suited after only slight adaptations thereof.

With the method of the initially defined kind, according to the invention this object is achieved by a combination of the following measures:

that the substrate, without a preceding sterilization, is led commonly with Zymomonas mobilis cells through a plurality of fermentation stages, i.e. at least three, that in each fermentation stage a concentration of at least 4 % by volume of ethanol is maintained, that the residence time of the fermentation medium consisting of a substrate and Zymomonas mobilis cells in the entire system is adjusted to a maximum of 3 ⅓ h, preferably to from 0.8 to 2.5 h, and that the dilution rate of the fermentation medium in the overall system is adjusted to a minimum of 0.3 $h^{-1}$, preferably to from 0.4 to 1.25 $h^{-1}$, that the Zymomonas mobilis cells are separated by sedimentation after the last fermentation stage and are recycled to the first fermentation stage, and that the ethanol-containing substrate separated from the Zymomonas mobilis cells is drawn off.

For the individual fermentation stages, fermentors connected in series, preferably three to six fermentors, are provided. In this manner it is possible to individually adjust the alcohol and substrate concentrations for the individual stages. Also the temperature is separately controllable in each stage. The sugar-containing substrate continuously flows through all fermentation stages, the sugars being gradually fermented. Additional substrate and an agent for controlling the pH-value, e.g. lye, may be added in doses to each fermentor or each fermentation stage, if necessary, so that a maximum productivity is achieved by accurately adapting the ratio of microorganism population to the alcohol and sugar concentrations in each stage. For this purpose, a certain excess of substrate may be maintained in all the fermentors. That is just what is not possible in a one-stage fermentation procedure, since in that case the sugars contained in the substrate must be fermented as far as possible so as to avoid losses.

Suitably, the substrates are supplied having high sugar contents, which has the advantage that the former are storable over longer periods of time without having to be afraid of a microbial infection. Aqueous dilution medium is added in the first fermentation stage only. A resulting sugar concentration of the substrate of approximately 15 % has proved to be particularly favorable.

*Zymomonas mobilis* is able to ferment sugars such as glucose, fructose and sucrose that are, e.g., contained in molasses, starch and cellulose hydrolysates.

The substrate furthermore contains nutritive salts, such as ammonium sulfate, as well as vitamins in a known manner and amount. As a further positive side effect of the method of the invention it has shown that one can do almost completely without the usual addition of very expensive yeast extract and can use corn steep liquor in its place.

At a pH of between 4.5 and 7, *Zymomonas mobilis* has the best growth conditions (cf. "Ethanol production by *Zymomonas mobilis*" in Advances in Biochemical Engineering, Vol. 23, p. 37).

Below a pH of 4, a pronounced growth inhibition already occurs, and at a pH of approximately 3, the bacterium completely stops reproducing. The most favorable pH range for a fermentation with *Zymomonas mobilis* thus lies between 4.5 add 6.0; a pH of approximately 5.0 is optimal. In such a slightly acidic medium practically only lactic bacteria and yeasts have favorable living conditions. An infection by other microorganisms is very little likely if pH values of 7 or slightly therebelow are avoided. Lactic bacteria, however, are already clearly damaged from an ethanol concentration of approximately 4 % by volume onwards, although heterofermentative types themselves excrete ethanol as metabolic product.

Yeasts grow the best at pH values of from 4 to 6, and their ethanol tolerance and temperature sensitivity are almost the same as those of *Zymomonas mobilis*.

However, *Zymomonas* is strictly anaerobic and is damaged by oxygen. Although yeast can also grow and ferment completely without oxygen, it tolerates oxygen on the other hand and is stimulated to an increased cell formation thereby. This can be seen quite clearly from the specific growth rates of aerobically and anaerobically grown yeasts. While a yeast of the type *Saccharomyces* grown without oxygen has a specific growth rate of approximately 0.15 $h^{-1}$, the same yeast has a growth of 0.25 $h^{-1}$ under aeration, thus growing almost twice as fast. Anaerobically, *Zymomonas mobilis* grows approximately as fast as aerated yeast; with a longer access of oxygen, the bacterium even dies.

For taking advantage of the reduced growth rate of yeasts relative to *Zymomonas mobilis* under anaerobic conditions for preventing infections, a further combination characteristic according to the invention is the adjusting of a short residence time or a high dilution rate of the fermentation medium in the overall system of the fermentation stages or fermentors. Due to the high flow rates, the occurrence of yeasts is prevented by practically washing out the infecting cells. For instance, at a residence time of 2 h in the entire system the flow rate is more than three times too high for the occurrence of yeast. Furthermore, by this procedure an especially high production of ethanol is obtained.

A part of the *Zymomonas mobilis* floc remains in the individual fermentation stages, even if the entire system has reached the state of equilibrium with a constant continuous flow. A smaller portion of the floc that depends on the residence time observed is delivered from the stages and moved to the respective next stage. After the final fermentation stage, the floc carried on by the substrate is separated, the separation from the substrate being effected in the simplest way, by sedimentation. With this separation made feasible by the use of flocculent *Zymomonas mobilis* strains, a large amount of undesired microorganisms possibly contained in the fermentation medium is removed from the system with the supernatant ethanol-containing substrate, whereas with a separation by centrifugation or filtration, all the foreign organism would be recycled together with *Zymomonas mobilis*.

According to a preferred embodiment of the method of the invention, at least a part of the $CO_2$ formed in the individual fermentation stages is circulated in each stage.

Therein, the $CO_2$ is withdrawn from the gas space of the fermentors and preferably is re-fed into the fermentors finely distributed from below, in which fermentors the gas flows through the fermentation medium and there causes a uniform distribution of the *Zymomonas mobilis* floc. Furthermore, any possible deposits in the bottom region of the fermentors are prevented in this manner.

For ensuring as uniform a distribution of the floc in the entire fermentation space as possible, is has also proved favorable to draw off the fermentation medium from the bottom of each of the individual fermentors and to feed it to the top of the next fermentor.

A further preferred embodiment of the method of the invention resides in that at least a part of the distillery slops remaining after recovery of the ethanol from the drawn-off ethanol-containing substrate is recycled into the first fermentation stage.

The ethanol recovery is effected, e.g., by rectification of the drawn-off fermented substrate whose ethanol content in most cases amounts to approximately 9 to 10 % by volume. The distillery slops remaining, which, due to the heating occurring during the rectification, are nearly sterile, still contains nutrient residues that can be used by the microorganisms if the distillery slops are recycled. Furthermore, in this manner the fresh water demand is lowered. The recycling is, however, limited in that the content of the substrate of unusable substances carried along in the distillery slops must not rise too high.

The method according to the invention will now be explained in more detail by way of the following examples and the drawing.

Example 1:

The fermentation process was carried out in three stages in a plant schematically illustrated by the drawing.

Three closed, substantially cylindrical fermentors connected in series are denoted by 1a, 1b and 1c in the drawing. Slightly above the bottom of the fermentors, a gas distributing means, e.g. a glass frit 2a, 2b and 2c, is each installed. Upon the third fermentor 1c, a sedimentation vessel 3 follows, which has the same construction as the fermentors, yet which has a conically downwardly tapering bottom part.

A concentrated sugar-containing substrate can be fed to the fermentors 1a, 1b and 1c via a duct 4, the branch ducts being each provided with closing means 5a, 5b and 5c. Furthermore, a lye duct 6 is provided, from which also branch ducts lead to the fermentors 1a, 1b and 1c.

In each of these branch ducts, there is a feed control 7a and 7b and 7c. As the feed controls, e.g. solenoid valves are suited, which may be controlled by pH-measuring probes (not illustrated) in the fermentors. The first one of the fermentors connected in series, 1a, in addition contains a feed 8 for fresh water or recycled distillery slops. From the gas space of each of the fermentors 1a, 1b and 1c, a gas duct leads to the gas distribution means 2a, 2b and 2c provided in the bottom part of the respective fermentor, via a compressor 9a, 9b and 9c.

For discharging excessive gas amounts, a gas discharge charge duct also provided with closing means 10a, 10b, 10c and 10d is installed in the top part of each fermentor 1a through 1c and the deposit container 3. The biomass collecting in the conically designed bottom part of the deposit container 3 is recycled to the top part of the first fermentor 1a by means of a pump 11 via the thick matter duct 12. The fermentation medium is each conducted away from the bottom part of the fermentors 1a and 1b and fed through ducts 13 and 13' to the top part of the next fermentor 1b and 1c, c, respectivley, and from the bottom part of the fermentor 1c to the top part of the sedimentation vessel 3, via duct 13''. The ethanol-containing substrate is drawn off from the sedimentation vessel 3 via the overflow duct 4. For thermosetting, all the fermentors and the sedimentation vessel may be provided with a double shell not illustrated, through which a heat transfer medium flows.

The fermentors and the sedimentation vessel of the plant used had an inner diameter of approximately 12 cm and a height of approximately 55 cm; their filling volume amounted to 5 l each. As the gas distribution means, a glass frit was installed slightly above the bottoms of the fermentors, and all the fermentors as well as the deposit container were provided with double shells.

At the start of the fermentation process, a nutrient and vitamin containing substrate having 15 % of sugar was provided in all the fermentors and in the sedimentation vessel, glucose, inverted sucrose or a starch hydrolysate having been used equally successfully for preparing the substrate. The air contained in the containers was removed by flushing with $CO_2$ or nitrogen, and the entire system was inoculated with approximately 70 g of *Zymomonas mobilis* floc. This bacterial culture had been grown in a prefermentation, because according to experience it takes a few days until the floc is actually formed after an inoculation of the substrate with a flocculating strain of *Zymomonas mobilis*.

After the inoculation, the system was left without supply of substrate until an intensive gas development started and the ethanol concentration in each fermentor had reached approximately 4% by volume. The $CO_2$ formed in the fermentation stages was circulated in each stage or in each fermentor via the compressors 9a, 9b and 9c.

Thereupon, the supply of concentrated substrate and dilution medium was started. The initial settings were 150 ml of substrate with 60 % of sugar/h and 750 ml of fresh water/h in the first fermentor 1a, as well as 100 ml of substrate with 60 % of sugar/h in the second fermentor 1b, so that as a result a sugar concentration of 15 % was adjusted at a total passage of 1 l/h. Although the substrate had initially been adjusted to a pH of 5.0, lye had to be added continuously for maintaining that pH, because an acidification of the fermentation medium occurred as a consequence of the uptake of $NH_4+$ from the ammonium sulfate contained in the substrate by the organisms.

By an intensive recycling of the bacterial fLoc collecting in the bottom part of the sedimentation vessel 3, the biomass concentration was continuously increased so as to finally be at a balance of between 20 and 25 g of dry substance/l. Due to the high specific productivity of *Zymomonas mobilis* it was thereupon possible to increase the total supply of substrate from 1 l/h to 6 l/h, without detecting unfermented sugar in the fermentation medium after the third fermentor 1c. In the fermented substrate from the overflow duct 14, 9.0 to 9.2 % by volume of ethanol were measured corresponding o a yield of from 93 to 95 % of theory.

Thus, with an addition of substrate of 6 l/h and an effective fermentation volume of 15 l (3×5 l; residence time in the entire system thus 2.5 h) there results a volumetric productivity of approximately 36 l of ethanol/$m^3$. h.

Even higher productivities are attainable with the plant disclosed. If, however, industrial scales are considered, the removal of the fermentation heat from the correspondingly larger containers at an even higher flow rate already constitutes a problem that is difficult to solve.

In the pilot plant disclosed, the fermentation was continuously carried out for three weeks. No infection problems occurred, although neither the substrate concentrate nor the dilution liquid had been sterilized.

COMPARATIVE EXAMPLE 1:

As disclosed in the preceding Example, the system was run up and then, at a total supply of substrate of 6 l/h, the pH control was switched off. Because of the abovementioned acidification due to an $NH_4+$ uptake of *Zymomonas mobilis*, the pH of the fermentation medium gradually sank and finally reached a value of 2.8. As a first reaction of the system, unfermented sugar occurred in the overflow 14, so that the flow rate had to be reduced. After approximately 30 h, the first yeast cells could be detected in the microscope, which cells reproduced continuously and finally could also be found in the bacterial floc. After the flow rate had to be reduced to only 0.6 l/h, the fermentation was stopped.

COMPARATIVE EXAMPLE 2:

As described above, the system was run up to an optimal output, and subsequently air was blown in via the frits 2a, 2b and 2c instead of the $CO_2$ formed. As the first effect, it was found that the ethanol yield sank to clearly below 90 %, probably due to an increased formation of byproducts, such as acetic acid or acetic aldehyde. Subsequently, also the flow rate had to be reduced, which again had the consequence that - also aided by the supply of oxygen - yeast cells occurred in the fermentation medium.

Contrary to the Comparative Example 1, the optimal operating condition of the system could be restored again by stopping the supply of air, and supplying $CO_2$ again. This was possible because, contrary to the course of the method according to Comparative Example 1, the bacterium *Zymomonas mobilis* was not irreversibly damaged, but only subjected to less favorable conditions. After the supply of air had been stopped, at first the yield improved again, the flow rate could be increased, and after approximately 40 h all the yeast had been flushed out of the system again.

What we claim:

1. A method of continuously producing ethanol from sugar-containing substrates comprising fermentation of the sugar in said substrates by a flocculating strain of *Zymomonas mobilis* cells under anaerobic conditions, the method consisting essentially of:
  flowing a fermentation medium comprising said substrates and said *Zymomonas mobilis* cells through at least three fermentation stages of a fermentation system without preceding sterilization;
  maintaining a concentration of at least 4% by volume of ethanol and a pH of about 5 in each of said fermentation stages;
  maintaining a residence time of said fermentation medium in said fermentation stages of up to about 3 h., corresponding to a dilution rate of said fermentation medium in said fermentation stages of at least about $\frac{1}{3}h^{-1}$;
  separating the *Zymomonas mobilis* cells after the final fermentation stage by sedimentation to form ethanol-containing substrates, and recycling said *Zymomonas mobilis* cells into the first fermentation stage; and
  removing said ethanol-containing substrates separated from said *Zymomonas mobilis* cells.

2. A method as set forth in claim 1, wherein said residence time of said fermentation medium in said fermentation stages is adjusted to from 0.8 to 2.5 h corresponding to a dilution rate of said fermentation medium in said fermentation stages of from 0.4 to 1.25 $h^{-1}$.

3. A method as set forth in claim 1, wherein $CO_2$ is formed in each one of said at least three fermentation stages and wherein at least a part of the $CO_2$ formed is circulated in the respective stage.

4. A method as set forth in claim 1, wherein ethanol is recovered from said drawn-off ethanol-containing substrate and distillery slops remain, and wherein at least a part of said distillery slops is recycled into the first one of said at least three fermentation stages.

5. A method as set forth in claim 1 wherein additional substrate is added to each stage as required to adapt the ratio of microorganism population to the alcohol and sugar concentration in each stage.

6. A method as set forth in claim 1 wherein a pH adjusting dent is added to each stage as required to control the pH.

7. A method as set forth in claim 6 wherein said substrate contains ammonium sulfate, the ammonium ions being taken up by the *Zymomonas mobilis* organisms, and said pH adjusting agent is lye.

* * * * *